(12) United States Patent
Chetrit et al.

(10) Patent No.: US 6,732,956 B1
(45) Date of Patent: May 11, 2004

(54) SPECIFIC DENTAL WATER PULSE CAPABLE OF BEING CONNECTED TO A RUNNING WATER FAUCET SPOUT

(76) Inventors: Michaël Chetrit, 121, avenue Foch, Fontenay sous Bois (FR), 94120; Emmanuel Cohen, 5 bis, rue du Louvre, Paris (FR), 75001; Yaun Chetrit, 29 square Saint Charles, Paris (FR), 75012

( * ) Notice: Subject to any disclaimer, the term of this patent is extended or adjusted under 35 U.S.C. 154(b) by 291 days.

(21) Appl. No.: 10/019,728
(22) PCT Filed: Jun. 30, 2000
(86) PCT No.: PCT/FR00/01869
§ 371 (c)(1),
(2), (4) Date: Dec. 26, 2001
(87) PCT Pub. No.: WO01/01882
PCT Pub. Date: Jan. 11, 2001

(30) Foreign Application Priority Data

Jun. 30, 1999 (FR) .............................................. 99 08355

(51) Int. Cl.$^7$ ................................................. B05B 7/06
(52) U.S. Cl. ...................... 239/428.5; 239/25; 239/438; 239/443; 239/289; 601/165
(58) Field of Search ........................ 239/25, 26, 428.5, 239/438, 443, 445, 446, 447, 289; 601/162, 163, 164, 165

(56) References Cited

U.S. PATENT DOCUMENTS

| | | | | |
|---|---|---|---|---|
| 3,227,380 A | * | 1/1966 | Pinkston | 239/428.5 |
| 3,468,306 A | * | 9/1969 | Heitzman | 601/165 |
| 4,133,482 A | * | 1/1979 | Moret | 239/381 |
| 4,138,064 A | | 2/1979 | Moret | |
| 5,385,533 A | | 1/1995 | Coviello | |
| 5,387,182 A | * | 2/1995 | Otani | 601/165 |
| 5,799,987 A | * | 9/1998 | Sampson | 285/81 |

* cited by examiner

*Primary Examiner*—Robin O. Evans
(74) *Attorney, Agent, or Firm*—Fenster + Company

(57) ABSTRACT

The invention concerns a dental water pulse operating on a running water pipe system as it can be connected to a running water faucet spout (3) and an anti-splash aerator. Said combination is characterised in that it comprises an upstream connection permanently screwed on the running water faucet spout whereof the shell (7) which enables to house an integral water aerating module (8), on its outer surface (in particular to maintain the height and standard diameter of the aerator), a connection system with pins and notches, connection system wherein the pins (5) of one of the parts of the connection system, upstream or downstream, are urged to be housed in the corresponding notches (16) of the other part, the pins or notches being integrated on the outer surface of the shell of the anti-splash aerator (7), whereon the dental water pulse downstream connection (4) is quick connected, downstream connection which, when connected to the anti-splash aerator (7) shell, diverts the water towards a tube (2), which is itself connected to the water pulse nozzle (1), to deliver a pressurised water jet (6), one or several ring type joints (10) providing a sealed connection between the dental water pulse downstream connection (4) and the anti-splash aerator (7) shell.

20 Claims, 3 Drawing Sheets

Figure 1:
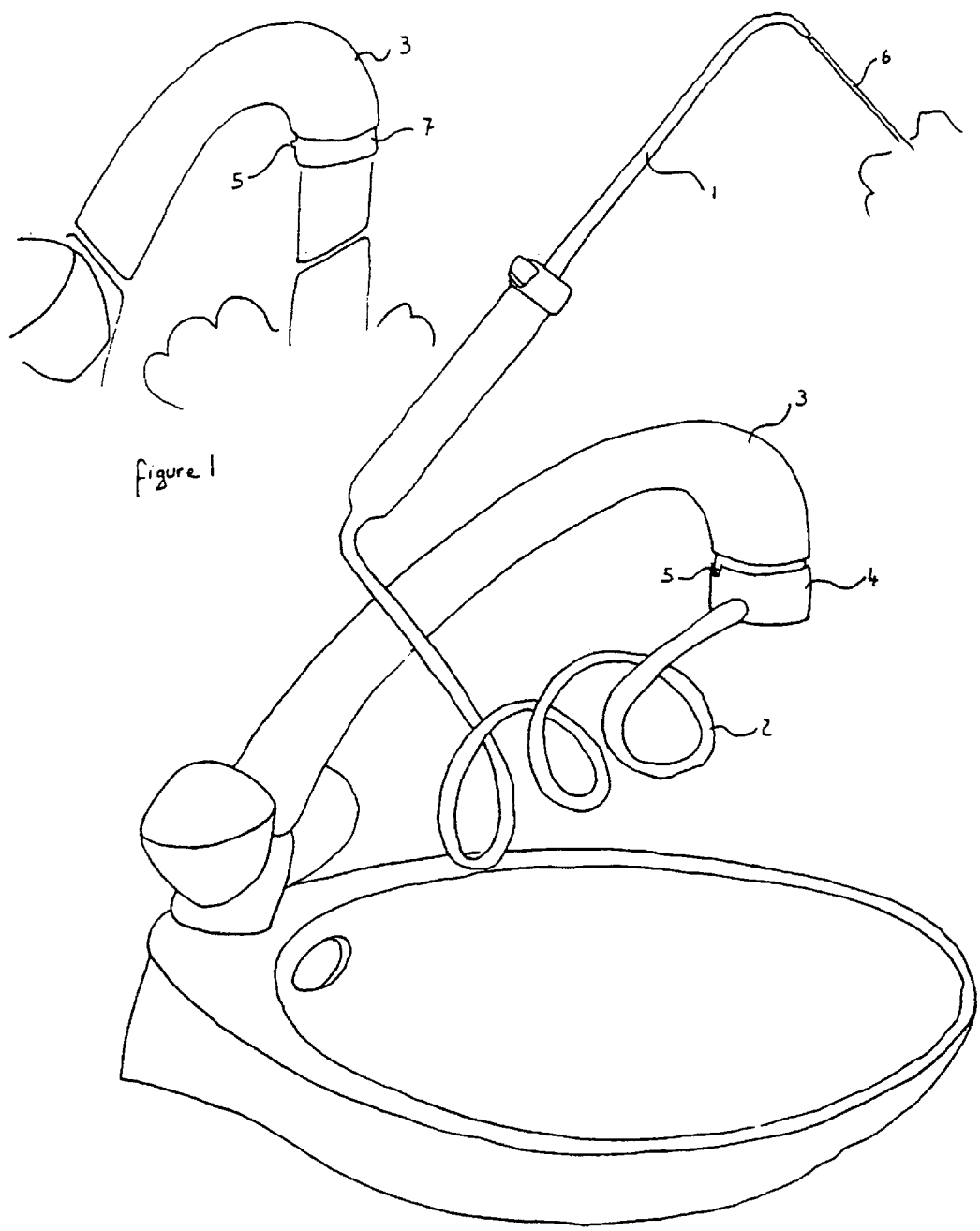

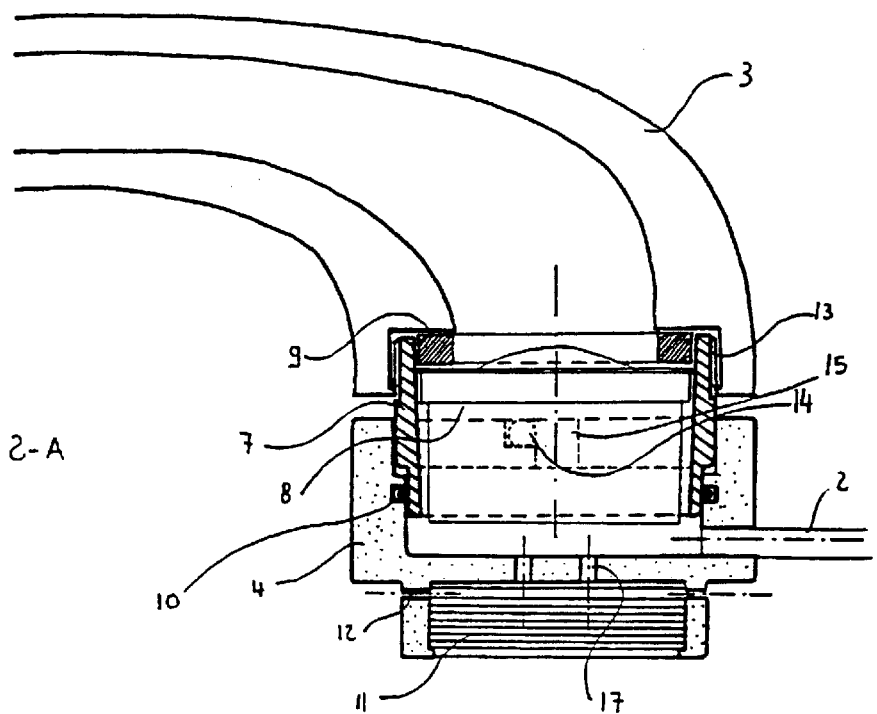
figure 2-A
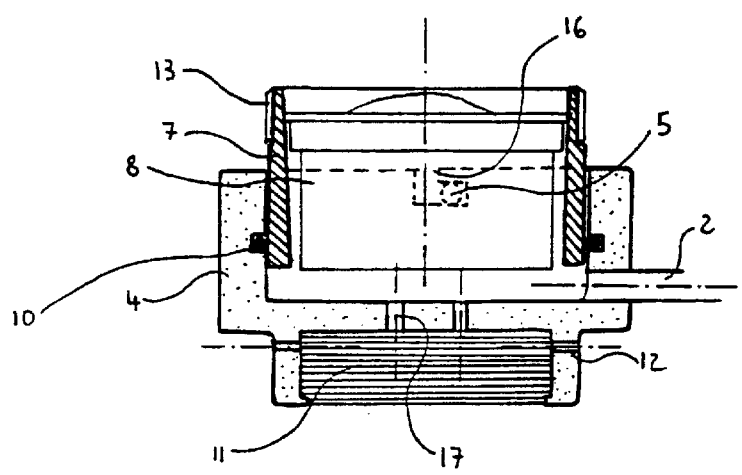
figure 2-B.

figure 3-A
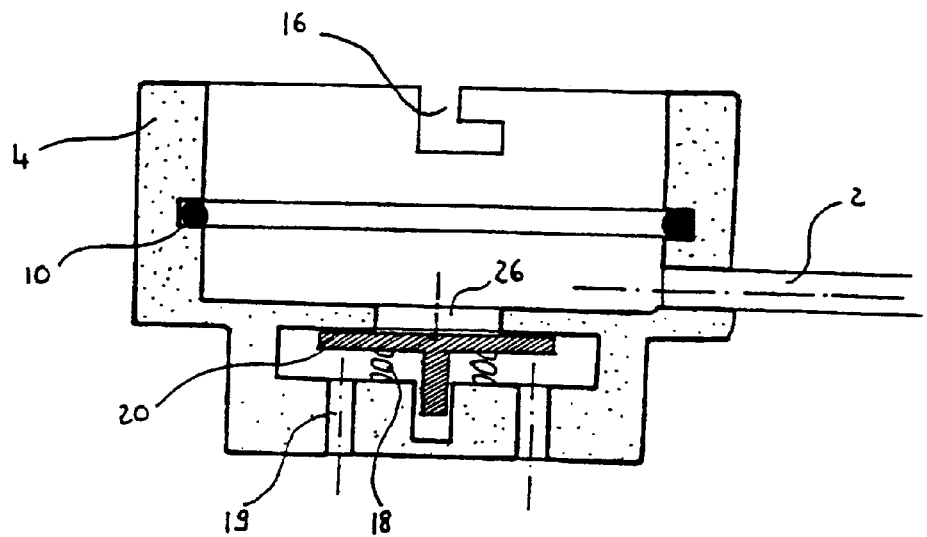
figure 3-B
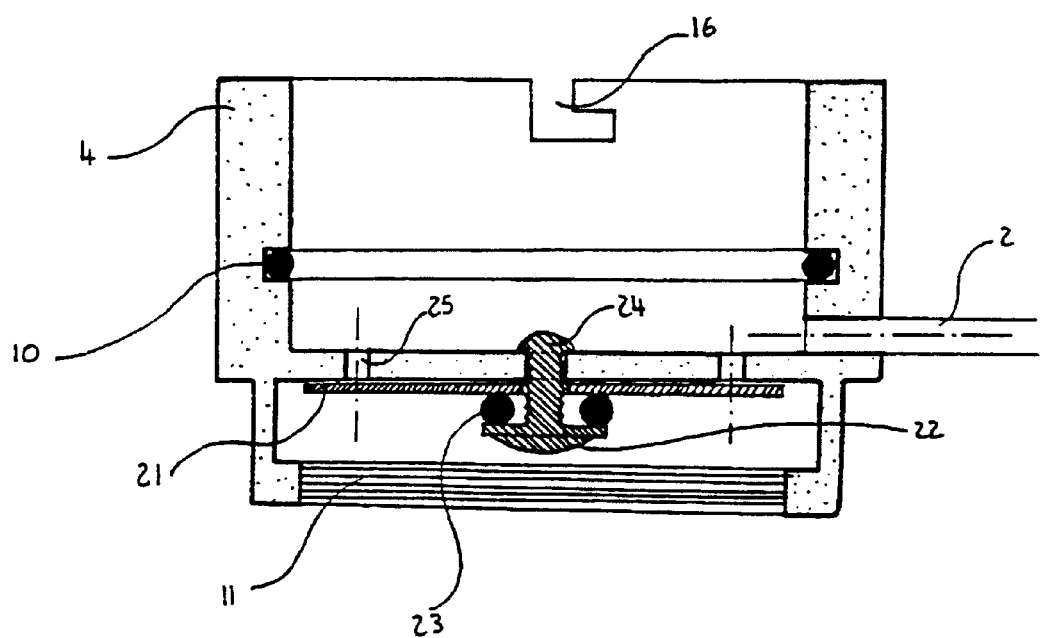

SPECIFIC DENTAL WATER PULSE CAPABLE OF BEING CONNECTED TO A RUNNING WATER FAUCET SPOUT

This application is a U.S. national filing of PCT Application No. PCT/FR00/01869, filed Jun. 30 2000.

The invention is a water pick for cleaning the interdental spaces which provides specific improvements for permitting its practical domestic use on the running water system after rapid connection to the spout of a faucet.

The principal objective of a water pick is to clean the interdental spaces that are difficult to reach with toothbrushes and where cariogenic food debris becomes deposited.

The market offers electric water picks but they are capable of being the source of electric shocks. They are also noisy, cumbersome, have a limited reservoir capacity and require preparatory operations (electrical outlet far from the washbasin, filling the reservoir and mechanical maintenance).

A water pick connected to the running water supply is an assembly formed by an attachment to the faucet spout (3), which deviates the running water toward a nozzle or orifice (1) at the exit of which a water jet (6) under pressure permits the cleaning of the interdental spaces (FIG. 1).

The concept of a water pick connected to a running water supply is not new.

However, the mechanisms developed hitherto were not conceived to be used in a practical, efficacious and rapid manner in the domestic environment of a bathroom.

The objective is thus to develop a water pick using a quick-connector, connectable and disconnectable quickly and easily at the spout of a running water faucet. Furthermore, an attempt is made to maintain the aerator function that permits the normal use of the faucet when the dental water pick is not connected. In effect, the aerator permits a uniform water flow, water economy, reduces the splashing and neatly stops the water flow when the faucet is shut off.

It will be assumed that an upstream connector (7) of the water pick is the part of the coupling fixed to spout of the running water faucet (3) and that the downstream connector (4) of the water pick is the part of the coupling fixed to the tube (2), which, in turn, is connected to the nozzle (1) of the water pick. The downstream connector (4) is connected to the upstream connector (7) to collect the water at the outlet of the running water faucet (3) and direct it toward the outlet of the nozzle (1).

The first concept consists in realizing the combination of a water aerator (7) screwed to the running water faucet spout and a dental water pick (FIG. 1). The shell of the water aerator screwed on the running water faucet spout thus integrates, on its external surface, a connection system that constitutes the upstream connector (7) of the dental water pick. The water aeration module (8) is accommodated in the upstream connector (7) of the water pick. The spout of the running water faucet (3) is supplied with male or female threads and therefore receive an aerator that can be screwed on, thanks to the mating male or female threads (13) on the shell of the aerator, an upstream connector (7) of the water pick, which permits the accommodation of an aeration module (8). When the dental water pick is not connected, the normal faucet function with aeration is preserved. This combination of aerator and water pick that can be used on a running water line thus effects a space-savings and a functionality important for the practical and effective use of a dental water pick connected to the spout of a running water faucet in a bathroom environment. One or more joints (9) assure a tight seal between the aerator and the running water faucet spout.

It is also very important that the upstream connector (7) of the water pick permanently screwed onto the faucet (3) be very inconspicuous. Its appearance should thus be as close as possible to a standard bathroom aerator.

An effective and economical technique consists in the use of connecting systems with catches and notches, such as the so-called "bayonet" or "clamp," for example. A system with notches and catches of the "clamp" type is, e.g., a clamp fixed to the downstream connector of the water pick and on which there are one or more notches (or catches), which are fitted in place during the clamping in one or more catches (or notches) located on the aerator shell.

The system used to route the downstream connector (4) of the water pick to the aerator shell (7) is integrated on the external part of the aerator shell to avoid resorting to a mobile or sliding aerator system (U.S. Pat. No. 5,385,533 A), in which the aeration module must be pushed into the aerator shell with each re-routing, which necessitates a greater height and diameter of the aerator shell, of the internal notches, cut into the thickness of the aerator shell, being, moreover, a system susceptible to becoming very easily furred, inhibiting the routing.

In the above-mentioned U.S. patent, the aerator slides and can thus become completely jammed in the upper position by turning slightly in its seat. The aerator can then no longer fulfill its normal role as aerator and is capable of very easily inhibiting the normal passage of water when the water pick is disconnected.

These shortcomings of the aforementioned U.S. patent filed nearly eight years ago remained concealed and were never ascertained.

In general, these systems require two or three catches on one of the two parts of the connector and the corresponding notches, L-type in the bayonet systems, for example, on the other part of the connector.

Here it was surprisingly found in tests that a single catch (5) barely one millimeter in diameter and a millimeter in length, perpendicular to the aerator shell (7), is sufficient to ensure maintaining the routing connection of the downstream connector to the water aerator shell, despite the water pressure in the device, once the catch (5) is engaged in the notch (16) of the downstream connector (FIG. 2-B).

One or more circular O-rings (10) around one of the two parts of the connector—the downstream connector ideally for greater inconspicuousness—assure the integrity of the seal of the connection.

One or more O-rings could preferentially encircle the aerator shell above the lower limit of the aerator base (either in the position of a screwed-on aerator, above the limit, or stopped, between the internal surface and the external surface of the aerator). Scale is capable of accumulating also on this limit (or stop).

For even more inconspicuousness, the cutting of the male or female threads of the aerator shell could be done so that this catch (5) is at the back of the faucet (3) in the position of a screwed-on aerator.

The notch(es) (15) can also be formed on the upstream connector and the corresponding catch(es) (14) on the downstream connector (FIG. 2-A).

To prevent the aerator shell (7) from becoming unscrewed from the spout of the faucet (3) when connecting the bayonet connector of the downstream connector (4) to the water aerator shell is effected, the clamping for the bayonet connection of the downstream connector on the aerator shell is made in the direction that contributes to the screwing of the aerator shell to the spout of the running water faucet (3).

The combination of the dental water pick and the aerator on the one hand and the economical, tightly sealed and inconspicuous system of the bayonet connector on the other, once joined, permits preserving the functionality of the faucet, as well as the external appearance. These decisive advantages for using a water pick connected to the spout of the running water faucet in a bathroom environment could not be included in the systems conceived to date. As important as cleaning the interdental spaces is for buccodental health, the dental water pick systems connected to the running water system to date and conceived for such a long time have not proven sufficiently functional and inconspicuous to permit their acceptance in the bathroom environment.

On the other hand, a third objective of the invention consists in obtaining a water jet with a lukewarm temperature at the outlet of the nozzle. In effect, the teeth are generally very sensitive to temperature.

The opening of the nozzle (1) exit is very narrow. The water flow rate is thus low. A strong predominance is then noted in one of the two water flows, the cold water flow and the hot water flow, the one whose pressure is greater in the faucet, even if the difference in pressure between the cold water flow and the hot water flow is very slight. The pressure of the cold and hot water flows is different in the great majority of sanitary installations. This difference is sometimes very important.

The idea is thus to manipulate one or more openings (17) in the connector, notably in the downstream part of the connector (4), to discharge part of the water into the sink in order to realize a sufficient flow rate and loss of water pressure to facilitate the mixing of the water flows and permit the rapid and easy obtention of tepid water. The flow rate and the loss of water pressure make the mixing of hot and cold water easier and more rapid, which is important to the user of a dental water pick that is to be connected to a water faucet spout.

In general, the pressure in the water lines varies in France from 2.5 to 8 bar. Some electric dental water picks can operate at higher pressures. However, the forces of the jet at the nozzle outlet should not be capable of injuring the gingival tissue. The flow rate and the loss of water pressure realized in the openings (17) in the connector thus also permit a reduction in the force of the jet at the nozzle outlet.

It can thus be important to adjust the pressure in the connector to a given value for limiting the force of the jet (6) at the outlet of the nozzle (1) to a given force. The invention also actualizes the combination of a dental water pick connector with a valve regulated so that the force of the jet at the nozzle outlet is limited to a maximum value.

Thus, if it is desirable to limit the pressure in the flexible tube (2) to three bar, it is possible to integrate into the connector a valve (20) that operates with a spring (18) calibrated to three bar. The excess flow is thus discharged into the sink through the openings (19) and (26) so that the pressure in the tube is three bar (FIG. 3-A).

This pressure limiting can also be realized with a weaker encumbrance, which is important, by placing a flexible membrane (21) against one or more openings (25) on the downstream connector (4) (FIG. 3-B). This flexible membrane (21) becomes curved and opens slightly with increasing pressure in the connector to discharge the excess flow to the sink through the openings (25). A screw (22) presses an O-ring (23) against the flexible membrane (21). The calibration of the system is notably a function of the deformation of the O-ring (23) by the screw (22). A rivet or adjusting nut (24) could maintain the adjustment of the screw (22) in the downstream connector (4). The initial deformation for obtaining a given calibration value will be determined empirically.

A splash guard (11) on the downstream connector will be able to direct the excess water to the sink. Air inlet holes (12) will facilitate the aeration of this excess water.

The components parts can be of any material, particularly plastic and/or metal.

What is claimed is:

1. Combination of a dental water pick (1), connectable to the spout of a running water faucet, and a water aerator (8), a combination that is comprised of an upstream connector (7) that can be permanently screwed onto the spout (3) of the faucet and that has an external surface overrunning the spout (3), said upstream connector (7) accommodating the aerator (8), and a removable downstream connector (4) for connecting the water pick (1), the downstream connector (4) and the upstream connector (7) cooperating by means of at least one catch (14,5) and at least one notch (15,16) as well as by means of seals (10), characterized in that the catch (14,5) or the notch (15,16) of the upstream connector (7) is provided on its external surface and that the aerator (8) is located in a fixed position inside upstream connector (7).

2. Combination according to claim 1, characterized in that the catch (14,5) or the notch (15,16) is singular.

3. Combination according to claim 1, characterized by the presence of at least one O-ring (10) surrounding, after connection, the external surface of the upstream connector (7) above the lower limit (the edge) of the surface of the upstream connector (7) containing the aerator (8), said O-ring(s) being fixed to the downstream connector (4) of the water pick and/or the upstream connector of the water pick.

4. Combination according to claim 1, characterized by charge loss openings (17) in either the upstream coupling (7) or downstream coupling (4), which evacuate a portion of the flow outside of the water pick.

5. Combination according to claim 1, characterized by a valve (20,21) in the downstream connector (4) to limit the water pressure in the connector.

6. Combination according to claim 5, characterized in that the valve is a membrane valve (21).

7. Combination according to claim 6, characterized in that the valve comprises a membrane (21) placed against one or more openings (25) via a screw (22).

8. Combination according to claim 5, characterized in that the valve is a valve (20) with a spring (18).

9. Combination according to claim 2, characterized by the presence of at least one O-ring (10) surrounding, after connection, the external surface of the upstream connector (7) above the lower limit (the edge) of the surface of the upstream connector (7) containing the aerator (8), said O-ring(s) being fixed to the downstream connector (4) of the water pick and/or the upstream connector of the water pick.

10. Combination according to claim 2, characterized by charge loss openings (17) in either the upstream coupling (7) or downstream coupling (4), which evacuate a portion of the flow outside of the water pick.

11. Combination according to claim 3, characterized by charge loss openings (17) in either the upstream coupling (7) or downstream coupling (4), which evacuate a portion of the flow outside of the water pick.

12. Combination according to claim 2, characterized by a valve (20,21) in the downstream connector (4) to limit the water pressure in the connector.

13. Combination according to claim 3, characterized by a valve (20,21) in the downstream connector (4) to limit the water pressure in the connector.

14. Combination according to claim 4, characterized by a valve (20,21) in the downstream connector (4) to limit the water pressure in the connector.

15. Combination according to claim 9, characterized by charge loss openings (17) in either the upstream coupling (7) or downstream coupling (4), which evacuate a portion of the flow outside of the water pick.

16. Combination according to claim 9, characterized by a valve (20,21) in the downstream connector (4) to limit the water pressure in the connector.

17. Combination according to claim 10, characterized by a valve (20,21) in the downstream connector (4) to limit the water pressure in the connector.

18. Combination according to claim 11, characterized by a valve (20,21) in the downstream connector (4) to limit the water pressure in the connector.

19. Combination according to claim 15, characterized in that the valve is a membrane valve (21).

20. Combination according to claim 19, characterized in that the valve comprises a membrane (21) placed against one or more openings (25) via a screw (22).

* * * * *